(12) United States Patent
Casanova et al.

(10) Patent No.: US 10,773,231 B2
(45) Date of Patent: Sep. 15, 2020

(54) METHOD FOR PRODUCING COLLOIDOSOME MICROCAPSULES

(71) Applicants: Universidad de Antioquia (UDEA), Medellín (CO); Nexentia S.A.S., Sabaneta (CO)

(72) Inventors: Herley Casanova, Medellín (CO); César Augusto Pérez Zapata, Medellín (CO)

(73) Assignees: Nexentia S.A.S., Sabaneta (CO); Universidad de Antioquia, Medellín (CO)

(*) Notice: Subject to any disclaimer, the term of this patent is extended or adjusted under 35 U.S.C. 154(b) by 41 days.

(21) Appl. No.: 15/737,832

(22) PCT Filed: Jun. 18, 2016

(86) PCT No.: PCT/IB2016/053638
§ 371 (c)(1),
(2) Date: Dec. 19, 2017

(87) PCT Pub. No.: WO2016/203454
PCT Pub. Date: Dec. 22, 2016

(65) Prior Publication Data
US 2019/0001294 A1    Jan. 3, 2019

(30) Foreign Application Priority Data
Jun. 19, 2015 (CO) .................................. 15-141752

(51) Int. Cl.
*B01J 13/08*    (2006.01)
*B01J 13/02*    (2006.01)
(Continued)

(52) U.S. Cl.
CPC ............ *B01J 13/08* (2013.01); *A23L 33/115* (2016.08); *A23P 10/35* (2016.08); *A61K 9/501* (2013.01);
(Continued)

(58) Field of Classification Search
None
See application file for complete search history.

(56) References Cited

U.S. PATENT DOCUMENTS 8,034,450 B2    10/2011    Curtis et al.
8,221,809 B2    7/2012    Subramanian et al.
(Continued)

FOREIGN PATENT DOCUMENTS

WO    2008118511 A1    10/2008
WO    2009037482 A2    3/2009
(Continued)

OTHER PUBLICATIONS

AD Dinsmore, MF Hsu, MG Nikolaides, M Marquez, AR Bausch, DA Weitz. "Colloidosomes: Selectively Permeable Capsules Composed of Colloidal Particles." Science, vol. 298, Nov. 1, 2002, pp. 1006-1009. (Year: 2002).*
(Continued)

*Primary Examiner* — Isaac Shomer
(74) *Attorney, Agent, or Firm* — The Morales Law Firm; Joseph L. Morales

(57) ABSTRACT

This invention relates to a process for colloidosome-type microcapsules elaboration from solid particles microcapsules obtained by ionic gelation. In the process, an (O/W) type emulsion is initially generated stabilized with the solid particles microcapsules, and then the particles are fixed to the interface by adsorption of polyelectrolytes, cross-linking, heat treatment or fatty coating, generating the colloi- (Continued)

Figure 1:
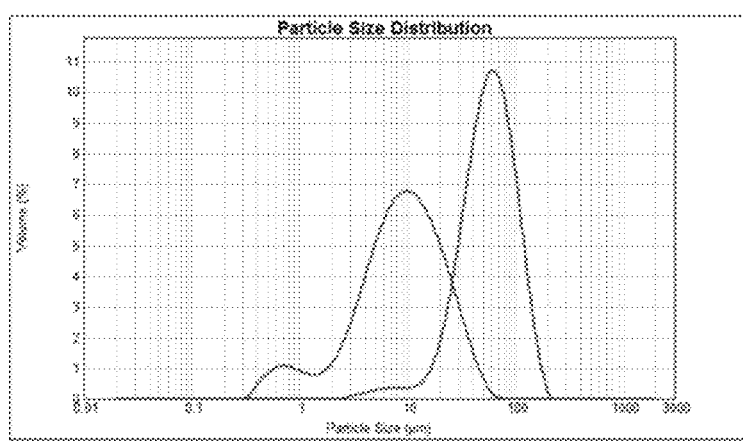

dosome with the water-insoluble phase encapsulated in the core and covered by the shell particles.

20 Claims, 25 Drawing Sheets

(51) Int. Cl.
 A23L 33/115 (2016.01)
 A23P 10/35 (2016.01)
 A61K 9/50 (2006.01)
 B01J 13/18 (2006.01)
 B01J 13/20 (2006.01)
(52) U.S. Cl.
 CPC .......... A61K 9/5015 (2013.01); A61K 9/5089 (2013.01); B01J 13/02 (2013.01); B01J 13/185 (2013.01); B01J 13/20 (2013.01); A23V 2002/00 (2013.01)

(56) References Cited

U.S. PATENT DOCUMENTS

| | | | |
|---|---|---|---|
| 10,085,948 B2 | 10/2018 | Casanova et al. | |
| 2004/0096515 A1 | 5/2004 | Bausch et al. | |
| 2009/0181254 A1 | 7/2009 | White et al. | |
| 2009/0191276 A1* | 7/2009 | Kim | B01J 13/02 424/499 |
| 2010/0047248 A1 | 2/2010 | Darvari et al. | |
| 2010/0234230 A1* | 9/2010 | Fowler | A01N 25/04 504/289 |
| 2016/0271071 A1* | 9/2016 | Casanova | A61K 9/5052 |

FOREIGN PATENT DOCUMENTS

| | | | | |
|---|---|---|---|---|
| WO | 2009091255 A1 | 7/2009 | | |
| WO | 2009148589 A1 | 12/2009 | | |
| WO | WO-2015028920 A1 * | 3/2015 | ............... | A61K 8/19 |
| WO | 2015071659 A1 | 5/2015 | | |

OTHER PUBLICATIONS

D Lee, DA Weitz. Double Emulsion-Templated Nanoparticle Colloidosomes with Selective Permeability. Advanced Materials, vol. 20, 2008, pp. 3498-3503. (Year: 2008).*
KL Thompson, P Chambon, R Verber, SP Armes. "Can Polymersomes for Colloidosomes?" Journal of the American Chemical Society, vol. 134, 2012, pp. 12450-12453. (Year: 2012).*
KL Thompson, SP Armes, JR Howse, S Ebbens, I Ahmad, JH Zaidi, DW York, JA Burdis. "Covalently Cross-Linked Colloidosomes." Macromolecules, vol. 43, 2010, pp. 10466-10474. (Year: 2010).*
C Wang, H Liu, Q Gao, X Liu, Z Tong. "Facile Fabrication of Hybrid Colloidosomes with Alginate Gel Cores and Shells of Porous CaCO3 Microparticles." ChemPhysChem, vol. 8, 2007, pp. 1157-1160. (Year: 2007).*
C Yuan, Y Xu, N Jiang, G Chen, B Xu, N He, L Dai. "Colloidosomes constructed by the seamless combination of nanoparticles: a mobile and recyclable strategy to intelligent capsules." Soft Matter, vol. 7, 2011, pp. 3366-3372. (Year: 2011).*
Y Chevalier, M-A Bolzinger. "Emulsions stabilized with solid nanoparticles: Pickering emulsions." Colloids and Surfaces A: Physicochemical and Engineering Aspects, vol. 439, 2013, pp. 23-34. (Year: 2013).*
F Nan, J Wu, F Qi, Y Liu, T Ngai, G Ma. "Uniform chitosan-coated alginate particles as emulsifiers for preparation of stable Pickering emulsions with stimulus dependence." Colloids and Surfaces A: Physicochemical and Engineering Aspects, vol. 456, 2014, pp. 246-252, available online May 21, 2014. (Year: 2014).*
OD Velev, K Furusawa, K Nagayama. "Assembly of Latex Particles by Using Emulsion Droplets as Templates. 1. Microstructured Hollow Spheres." Langmuir, vol. 12, 1996, pp. 2374-2384. (Year: 1996).*
KL Thompson, SP Armes, JR Howse, S. Ebbens, I. Ahmad, JH Zaidi, DY York, and JA Burdis. Covalently Cross-Linked Colloidosomes. Macromolecules, vol. 43, 2010, pp. 10466-10474. (Year: 2010).*
Ao, Z. et al., Colloidosomes formation by controlling the solvent extraction from particle-stabilized emulsions, Colloids and Surfaces: Physicochemical and Engineering Aspects, May 13, 2008, 592-596, 384 (2011).
Cayre, O.J. et al., Fabrication of novel colloidosome microcapsules with gelled aqueous core, Journal of Materials Chemistry, Sep. 16, 2004, 3351-3355.
Lisa M. Croll and Harald D.H. Stöver, Formation of Tectocapsules by Assembly and Crosslinking of Poly (divinylbenzene-alt-maleic anhydride) Spheres at the oil-water interface, Langmuir, May 8, 2003, 5918-5922, vol. 19, No. 14, 2003.
Croll, L.M., et al., Composite tectocapsules containing porous polymer microspheres as release gates, Macromolecules, Feb. 22, 2005, 2903-2910, vol. 38, No. 7. 2005.
Yannan Cui and Jeroen S. Van Duijneveldt, Microcapsules Composed of Cross-Linked Organoclay, Langmuir, Jan. 9, 2012, 1753-1757, vol. 28, 2012.
Dinsmore, A.D., et al., Colloidosomes: selectively permeable capsules composed of colloidal particles, Science, Nov. 1, 2002, 1006-1009, vol. 298, 2002.
Fujiwara, M., et al., Encapsulation of proteins into CaCO3 by phase transition from vaterite to calcite, Crystal Growth Design Article, Jul. 26, 2010, 4030-4037, vol. 10, 2010.
Guillot, S., et al., Internally structured pickering emulsions stabilized by clay mineral particles, Journal of Colloids and Interface Science, Feb. 24, 2009, 563-569, 333, 2009.
He, X.D., et al., The preparation of composite microsphere with hollow core/porous shell structure by self-assembling of latex particles at emulsion droplet interface, Journal of Colloid Interface Science, Mar. 9, 2006, 791-796, 299, 2006.
Samia Laïb and Alexander F. Routh, Fabrication of colloidosomes at low temperature for the encapsulation of thermally sensitive compounds, Journal of Colloid Interface Science, Oct. 22, 2007, 121-129, vol. 317, 2008.
Liu, G., et al., Rearrangement of layered double hydroxide nanoplatelets during hollow colloidosome preparation, Journal of Colloids and Interface Science, Sep. 3, 2009, 302-306, vol. 345, 2010.
Rossier-Miranda, F.J., et al., Microcapsule production by an hybrid colloidosome layer-by-layer technique. Food Hydrocolloids, May 2012, 119-125, vol. 27, 2012.
Rossier-Miranda, F.J., et al., Colloidosomes: Versatile microcapsules in perspective. Colloids and Surfaces A: Physicochemical and Engineering Aspects, Apr. 5, 2009, 43-49, vol. 343, 2009.
Sturzenegger, P.N., et al., Size and Microstructure Control of Calcium Aluminate, Journal of the American Society, Apr. 27, 2012, 1-10.
Velev, O.D., et al., Assembly of latex particles by using emulsion droplets as templates, Microstructured hollow spheres, Langmuir, May 15, 1996, 2374-2384, 12.
Wang, X., et al., Preparation of core-shell CaCO3 capsules via Pickering emulsion templates. Journal of Colloid Interface Science, Jan. 17, 2012, 24-31, 372.
Lui, H., et al., Fabrication of novel core-shell hybrid alginate hydrogel beads, International Journal of Pharmaceutics, Sep. 22, 2007, 104-112, 351 (2008).
Thompson, K.L., et al., Colloidosomes: Synthesis, properties and applications, Journal of Colloid and Interface Science, Dec. 8, 2014, 217-228, 447 (2015).
Quan-Xing, G., et al., Facile and high efficient fabrication of hybrid microcapsules for urease encapsulation and their use as biomimetic reactors, Chemical Research in Chinese Universities, Sep. 2010, 842-846, 26 (5).
Chilkawar, R.N., et al., Development and evaluation of colloidosomes of Glibenclamide, World Journal of Pharmaceutical Research, Jul. 2014, 933-946, 3(4).
Munin et al., Encapsulation of Natural Polyphenolic Compounds; a Review, Pharmaceutics, 2011, 3, 793-829.

* cited by examiner

METHOD FOR PRODUCING COLLOIDOSOME MICROCAPSULES

TECHNICAL FIELD

This invention relates to a process for the preparation of colloidosomes-type microcapsules, which employs nano- or microparticles of water-insoluble solids obtained by ionic gelation as an emulsifying material and microcapsule shell-forming. The particles that stabilize the emulsion are fixed at the interface by polyelectrolyte adsorption, cross-linking, heat treatment or treatment with fatty acid emulsions.

INVENTION BACKGROUND

A colloidosome is defined as a microcapsule whose shell is formed by colloidal particles (with particle sizes usually less than 1 μm), which are adsorbed on the encapsulated substance and subsequently stabilized forming a shell by its cross-linking, fusion or sintering (Rossier, 2009).

The first report of colloidosomes-type microcapsules elaboration corresponds to the Velev and cols (1996) work, which used latex particles to stabilize and form 1-octanol colloidosomes. The method called soft template (soft template, (Rossier-Miranda et al., 2009)), uses the emulsion droplets as the base on which the colloidal solid particles forming the shell are adsorbed generating greater control and adsorption efficiency. In the method called hard template (hard template) solid particles are used as the colloidosome template.

Dismore and cols (2002) made colloidosomes without pretreatment, using polymethylmethacrylate (PMMA) particles immersed in a continuous organic phase of decahydronaphthalene in the drops of water presence. This method allows controlling the temperature and the heating time to adjust the porosity and strength of the shell, achieving versatility in the release kinetics of the encapsulated compounds. However, the high vitreous transition temperature of PMMA (92-142° C.) limits its use in thermolabile systems.

Guillot (2009) and Fujiwara (2010) reported colloidosomes made from clay minerals (v.g. montmorilonite and Laponite) and sodium silicate in ammonium acid carbonate ($NH_4HCO_3$) presence, using a W/O/W double emulsion as template. The proposed procedures, although successful in the colloidosome-type particles formation, are very difficult to scale at the industrial level and are more profiled for academic applications that allow the study and characterization of structured systems at microscopic level.

Liu and cols (2010) reported the production of hollow colloidosomes using nanosheets of Mg/Al double hydroxide in layers (LDH for its acronym in English). The interface structure allowed to be modulated depending on the type of organic solvent used for the emulsified oil phase extraction. Even though this modulation type of the interface structure of the colloidosome-type microcapsule is a great prospect for food applications, the use of organic solvents and the long times required for the adsorption processes, make non-viable its scaling at an industrial level.

The document WO 2009091255 discloses a process where colloidal particles of triglycerides, monoglycerides or diglycerides, proteins and cells are used as emulsion stabilizers and proteins and/or polysaccharides to fix the shell by a coacervation process. The main disadvantage of this process is the mono, di and triglycerides use, which, when melted, destabilize the colloidosome shell.

Wang and cols (2012) elaborated $CaCO_3$ colloidosomes by sunflower oil emulsions generation and subsequent fixation of the solid particles in the shell, by $CaCO_3$ crystals coprecipitation by reacting $CaCl_2$) with $CO_2$ in-situ. The colloidosomes generated with this methodology showed high resistance to the system water evaporation, as well as delaying the flavors release. While this process is feasible to be scaled at the industrial level, high concentrations of NaCl as a byproduct are generated, which must be eliminated by an additional washing step.

The document WO2009/037482 discloses the colloidosome-type microcapsules elaboration, using sterically stabilized polymer particles in the emulsions elaboration with the subsequent formation of the shell by increasing the system temperature at a temperature higher than the polymer vitreous transition. In this process a lower particles adsorption is generated on the interface with the consequent instability of the system when drying.

The patent WO2009/148598 describes the microfluidization technology use for the stabilized drops elaboration with polymeric, colloidal or lipid particles with potential use as an encapsulating medium for interest substances. The main drawback of this process is the use of polymer particles that necessarily require heat treatment for its sintering and forming a stable shell.

Obviously, the prior art shows the need to develop and optimize processes for obtaining colidosomes-type microcapsules from materials with application in the food industry, in the cosmetics field or in the pharmaceutical area.

BRIEF INVENTION DESCRIPTION

This invention relates to a process for colloidosomes-type microcapsules preparation. By means of an ionic gelation process on nano- and micrometric solid particles, the surface chemistry of these particles is modified to produce emulsions of O/W type. The particles adsorbed on the emulsion drops are subsequently fixed by charged macromolecules adsorption and polyvalent ions addition, by heat treatment, or by cross-linking.

Once the particles are fixed, the suspension can be dried to obtain powder colloidosomes.

By means of the invention process, microcapsules are obtained by using shell-forming particles with a high adsorption on the oil-water interface, which allow increasing the efficiency of the emulsification process and the encapsulated material concentration.

BRIEF FIGURES DESCRIPTION

FIG. 1. Calcium carbonate particle size distribution superficially modified by ionic gelation: i) dry and agglomerated (red line); ii) milled and in aqueous suspension (green line) (Example 1).

Figure 2:
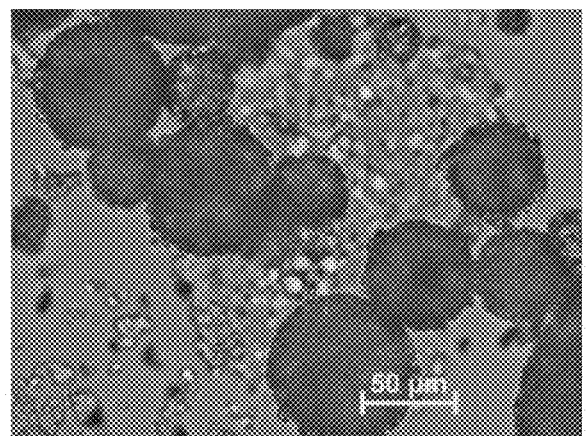

FIG. 2. Optical micrograph of oleic acid emulsion stabilized with calcium carbonate microparticles superficially modified by ionic gelation (Example 1).

Figure 3:
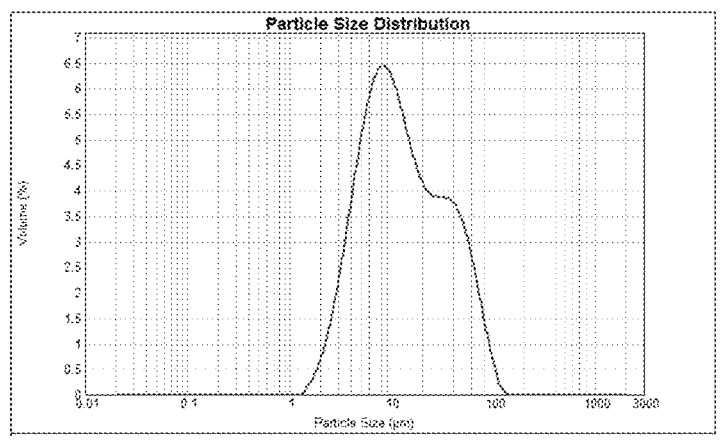

FIG. 3. Particle size distribution of oleic acid emulsion stabilized with calcium carbonate microparticles superficially modified by ionic gelation (Example 1).

Figure 4:
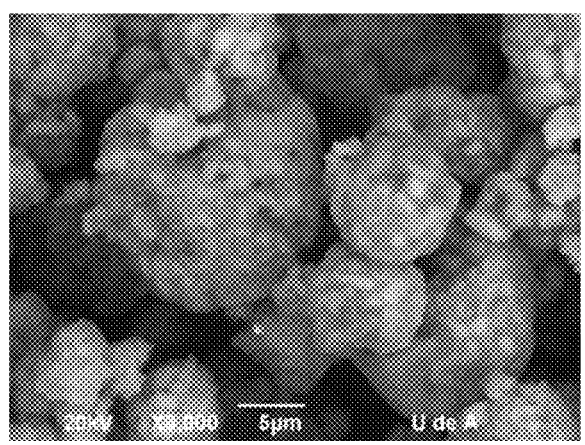

FIG. 4. Scanning electron microphotograph of oleic acid colloidosome with spray-dried calcium carbonate shell (Example 1).

Figure 5:
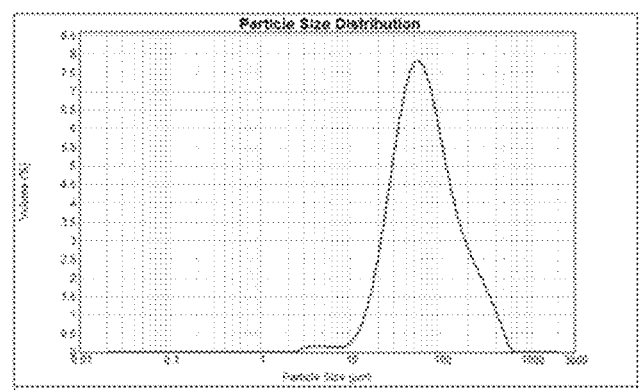

FIG. 5. Particle size distribution of oleic acid colloidosomes with spray-dried calcium carbonate shell (Example 1).

Figure 6:
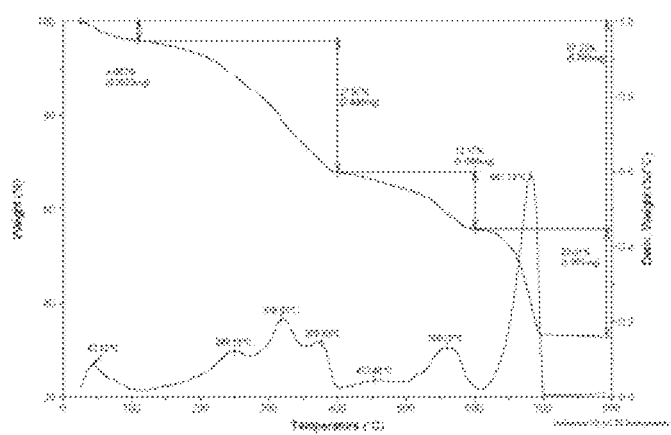

FIG. 6. Colloidosome thermogram of oleic acid with spray-dried calcium carbonate shell (Example 1).

Figure 7:
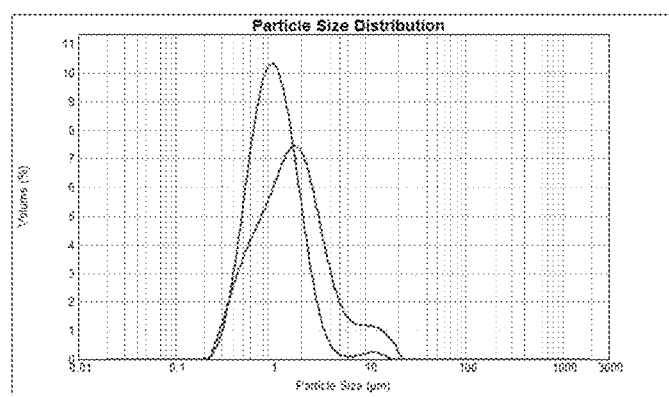

FIG. 7. Particle size distribution of sub-micrometer titanium dioxide superficially modified by ion gelation: i) dry and agglomerated (red line); ii) milled and in aqueous suspension (green line) (Example 2).

Figure 8:
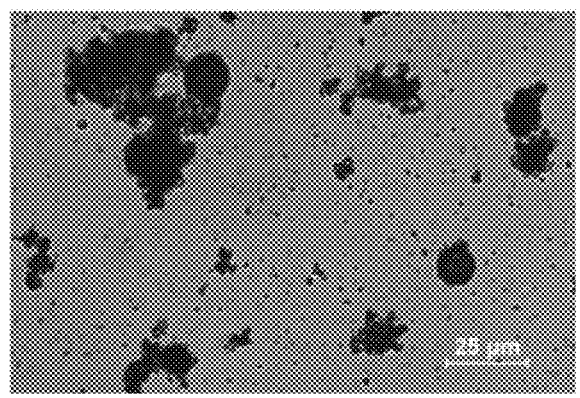

FIG. 8. Optical Micrograph of stabilized sunflower oil emulsion with sub-micrometric particles of titanium dioxide superficially modified by ionic gelation (Example 2).

Figure 9:
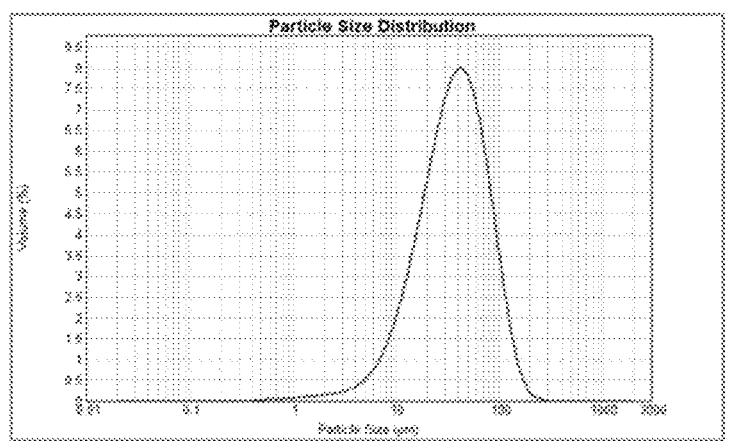

FIG. 9. Particle size distribution of stabilized sunflower oil emulsion with sub-micrometer titanium dioxide superficially modified by ionic gelation (Example 2).

Figure 10:
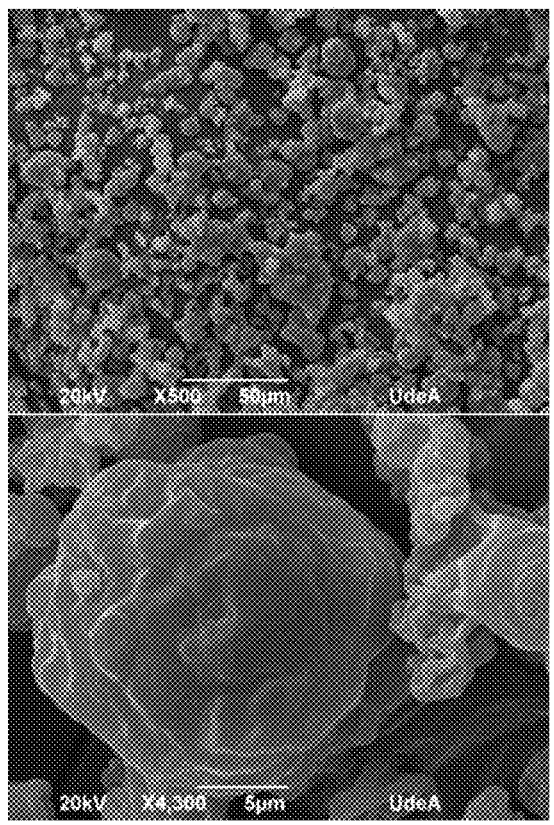

FIG. 10. Scanning electron micrographs of sunflower oil colloidosomes with spray-dried titanium dioxide shell (Example 2): left side increase of 500×, right side increase of 4300×.

Figure 11:
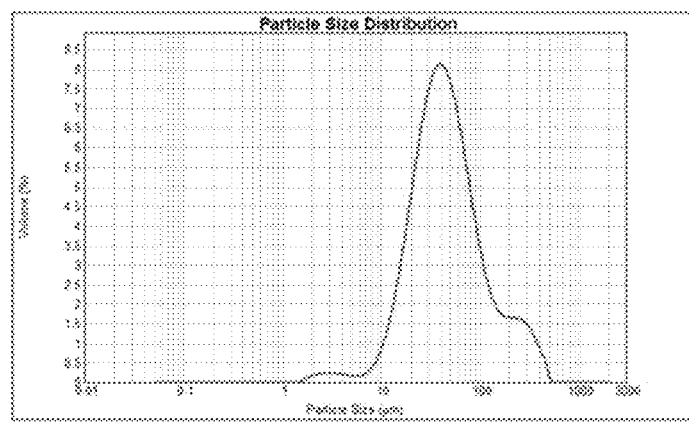

FIG. 11. Particle size distribution of sunflower oil colloidosomes with spray-dried titanium dioxide shell (Example 2).

Figure 12:
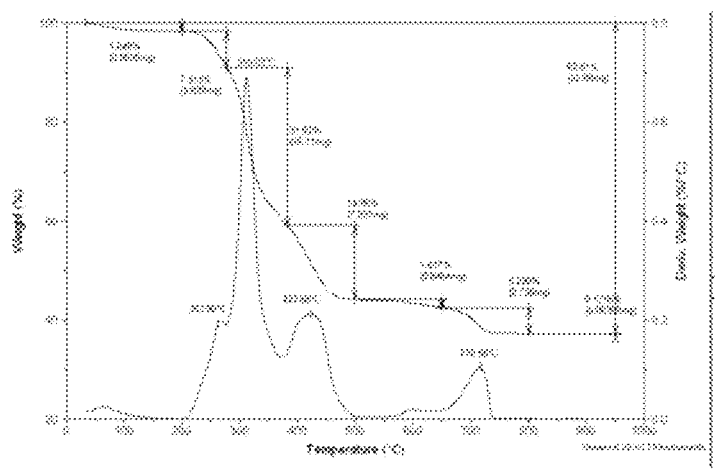

FIG. 12. Sunflower oil colloidosomes thermogram with spray-dried titanium dioxide shell (Example 2).

Figure 13:
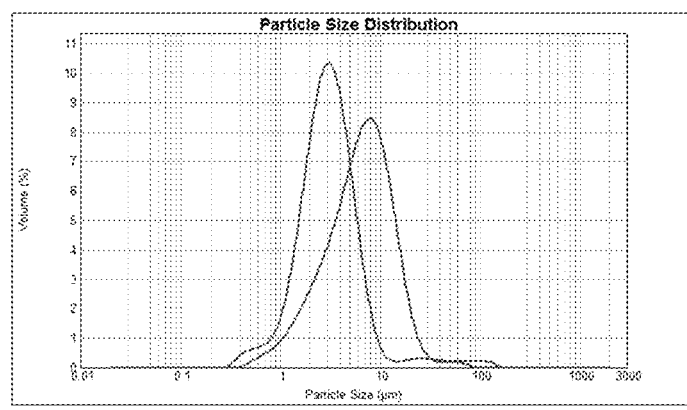

FIG. 13. Particle size distribution of micrometer calcium phosphate superficially modified by ionic gelation: i) dry and agglomerated (red line); ii) milled and in aqueous suspension (green line) (Example 3).

Figure 14:
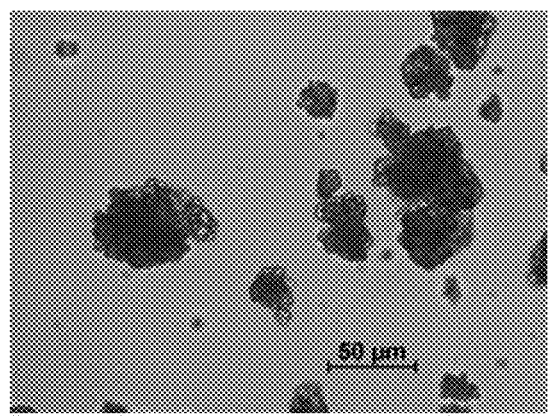

FIG. 14. Optical micrograph of mono and diglyceride mixture emulsion stabilized with micrometric calcium phosphate particles superficially modified by ionic gelation (Example 3).

Figure 15:
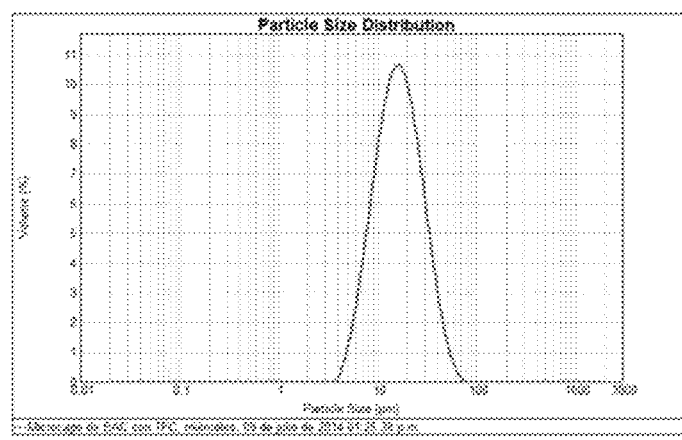

FIG. 15. Particle size distribution of mono and diglyceride mixture emulsion stabilized with micrometric calcium phosphate particles superficially modified by ionic gelation (Example 3).

Figure 16:
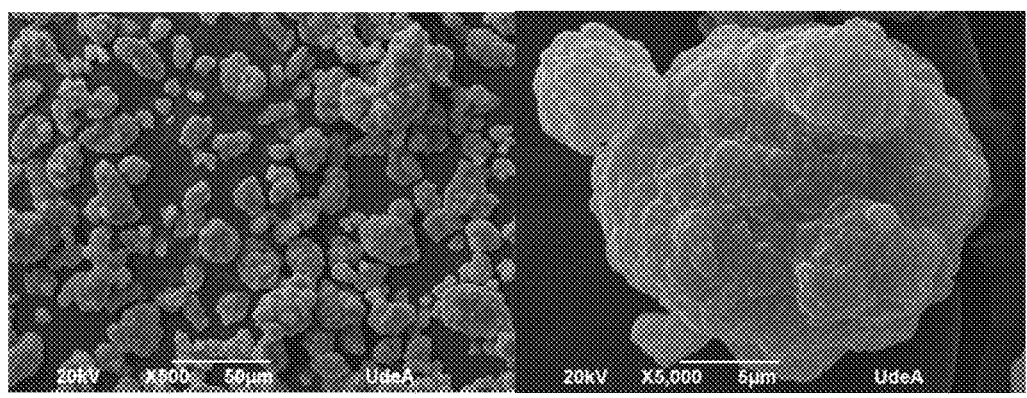

FIG. 16. Scanning electron micrographs of mono and diglyceride mixture colloidosomes with spray-dried calcium phosphate shell (Example 3): left side increase of 500×, right side increase of 5000×.

Figure 17:
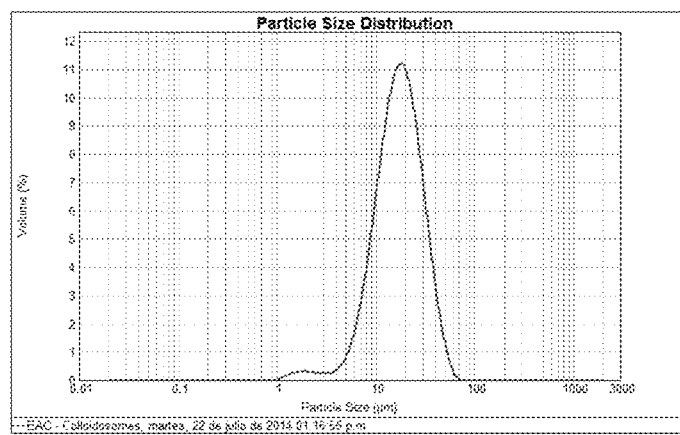

FIG. 17. Particle size distribution of mono and diglyceride mixture colloidosome with spray-dried calcium phosphate shell (Example 3).

Figure 18:
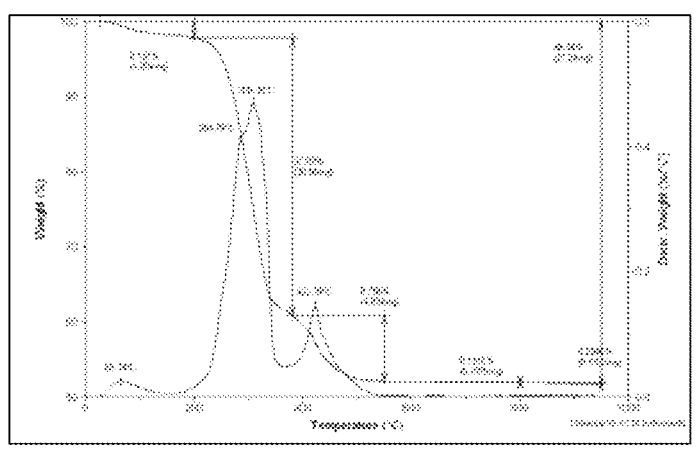

FIG. 18. Colloidosome thermogram of mono and diglyceride mixture with spray-dried calcium phosphate shell (Example 3).

Figure 19:
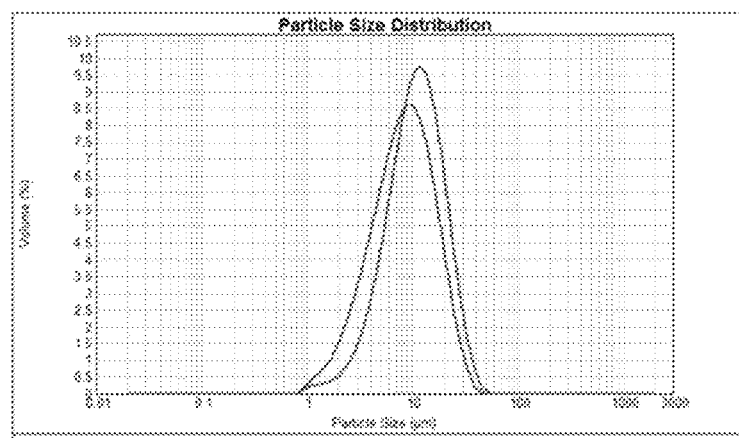

FIG. 19. Particle size distribution of micrometric kaolin superficially modified by ionic gelation: i) dry and agglomerated (red line); ii) milled and in aqueous suspension (green line) (Example 4).

Figure 20:
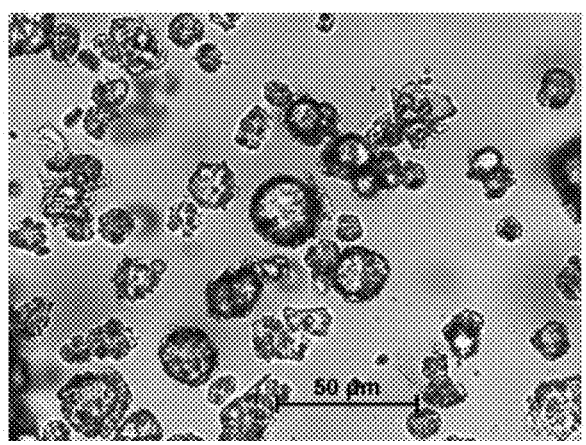

FIG. 20. Optical micrograph of canola oil emulsion stabilized with micrometric kaolin particles superficially modified by ionic gelation (Example 4).

Figure 21:
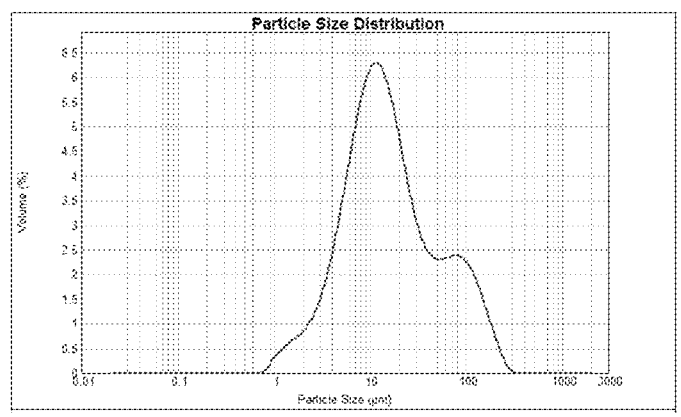

FIG. 21. Particle size distribution of canola oil emulsion stabilized with micrometric kaolin particles superficially modified by ionic gelation (Example 4).

Figure 22:
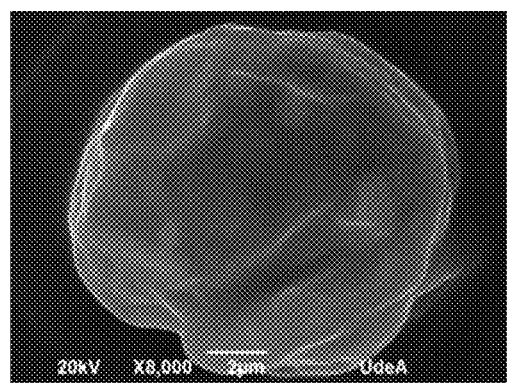

FIG. 22. Scanning electron micrograph of canola oil colloidosomes with spray-dried kaolin shell (Example 4).

Figure 23:
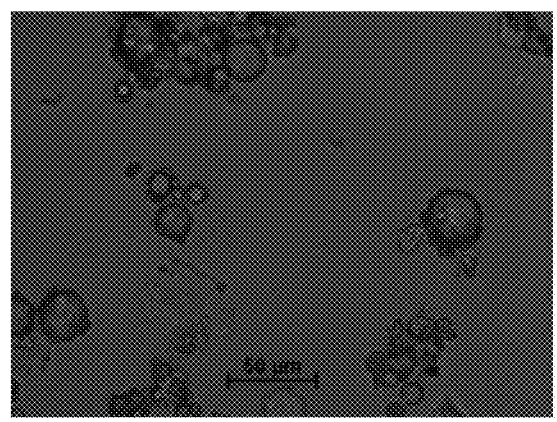

FIG. 23. Optical micrograph of stabilized canola oil colloidosome with kaolin micrometric particles superficially modified by ionic gelation and with fatty acid reinforcement (Example 4).

Figure 24:
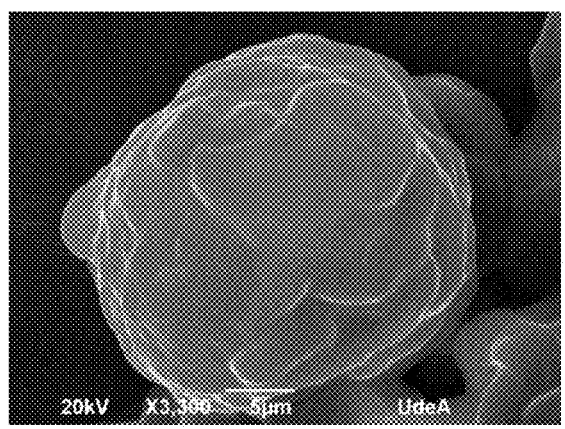

FIG. 24. Scanning electron micrograph of canola oil colloidosomes with kaolin shell, reinforced with fatty acids and spray-dried (Example 4).

Figure 25:
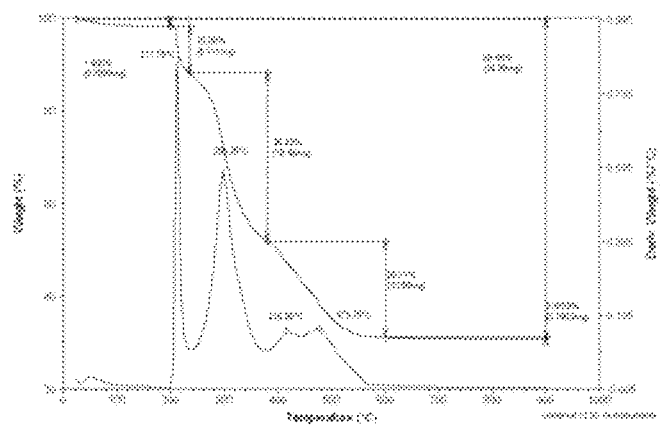

FIG. 25. Canola oil colloidosomes thermogram with kaolin shell reinforced with fatty acids and spray-dried (Example 4).

DETAILED DESCRIPTION OF THE INVENTION

This invention describes a process of making colloidosomes-type microcapsules of liquid phases insoluble in water, using nanoparticles, microparticles or their combination, superficially modified obtained by ionic gelation.

To obtain the colloidosome, an oil-in-water (O/W) emulsion is initially generated stabilized with nano- or solid microparticles insoluble in water and obtained by ionic gelation. The emulsion stabilized with the particles is produced by applying to the disruptive forces system such as shear, cavitation, collision between particles, pressure drop or the combination of two or more types of these disruptive forces.

Subsequently, the particles are fixed to the interface by polyelectrolytes adsorption, heat treatment, cross-linking, treatment with emulsion of a saturated fatty acid or fatty acids mixture, generating the colloidosome with the insoluble phase in water encapsulated in the core and coated by the shell particles. The colloidosomes obtained can have sizes between 100 nm and several millimeters. The mechanical stability of colloidosomes obtained in suspension makes it possible to carry out drying processes to achieve colloidosomes in the form of dry powder.

The process of ionic gelation on particles is achieved by polyvalent cations addition to an insoluble solids suspension, previous sub-environment thermal treatment that allows a controlled gelation of the charged macromolecules. The subsequent increase in temperature consolidates the shell formation over the insoluble solid particles. The detailed characteristics and conditions of the ionic gelation process are described in the document CO2013203104, which is incorporated in its entirety as a reference.

The suspension of solid particles treated superficially by ionic gelation is subsequently dried, generating particles agglomerates. These agglomerates are redispersed in water and subjected to a milling process, to generate individual particles that are used to emulsify a liquid phase insoluble in water by applying the mentioned disruptive forces.

The emulsion stabilized with the particles, requires the particles fixation in the liquid interface of the drops by polyelectrolytes adsorption, heat treatment, cross-linking, treatment with emulsion of a saturated fatty acid or fatty acids mixture, generating a colloidosome, where the insoluble phase in water corresponds to the core and the particles form the shell.

The colloidosomes typical diameters are between 100 nm and several millimeters. The wet system produces typically spherical colloidosomes with a liquid phase content insoluble in water between a 5% and 80%. The colloidosomes in aqueous suspension can be subsequently dried by spray drying, lyophilization, tray heating or other alternative drying methods. The polyelectrolytes adsorption, crosslinking or particles sintering degree, determines the shell mechanical properties, and consequently, its stability in the drying processes. Typically, colloidosomes can be dried at temperatures up to 250° C. without causing rupture of their shell.

The liquid phases colloidosomes elaboration process insoluble in water using particles superficially modified by ionic gelation of this invention, comprises the following steps:

a) develop a negatively charged polyelectrolytes solution, adjust the pH at a certain value between 5.0 and 8.0 and cool;

b) elaborate a suspension of insoluble solids in water, adjusting its pH;
c) mix the polyelectrolytes solution obtained in a) with the suspension of water-insoluble solids obtained in b), applying agitation to the system and controlling its temperature;
d) add a solution of polyvalent ions to the aqueous suspension obtained in c) and heat;
e) dry the aqueous suspension until get an agglomerated solid particles dry powder superficially modified;
f) redisperse the dry solid particles in water by applying disruptive forces to prevent the agglomerates formation;
g) emulsify an insoluble liquid in water using as emulsifier the suspension obtained in (f) and optionally bring the system temperature to more than 40° C.;
h) add a polyvalent cations solution to the emulsion stabilized by particles obtained in step (g);
i) add a solution of a polyelectrolyte negatively charged to the emulsion stabilized by particles obtained in step (h) generating colloidosomes in suspension;
j) repeat steps (h) and (i) to generate shells with greater mechanical stability;
k) optionally adding the emulsion stabilized by particles obtained in step (g) to an emulsion of saturated fatty acids to generate shells of greater mechanical stability; and
l) optionally drying the suspended colloidosome from step (j) or (k) to get powder colloidosomes. Optional drying of the colloidosome obtained in step (j) or (k) can be done in the presence of polyelectrolytes.

The characteristics of the colloidosomes elaboration process as well as the characteristics of the colloidosomes generated by said process are described in detail. These characteristics can be interchanged to describe both the process and the colloidosome.

Water insoluble solids are nanoparticles, microparticles or their combination, which preferably must generate surface charge when dispersed in water as a product of dissociation of their functional groups when interacting with water or another protic solvent. In a preferred modality, the insoluble solids for the ionic gelation process are metallic and non-metallic minerals or other insoluble solids such as phyllosilicates, polymer particles and insoluble solids obtained via synthesis, extraction or by bioprocesses.

The particle diameter of the water insoluble solid suitable for the ionic gelation process is between 100 nm and several millimeters. Compact solid particles are preferred for the surface modification by ionic gelation process, although other morphologies can also be employed. The solids concentration in the system is usually lower than 80%.

The shell-forming polyelectrolytes are typically proteins, polysaccharides or synthetic polymers negatively charged. In a preferred modality, the proteins include milk proteins, vegetable origin proteins, gelatin, albumins and mixtures thereof. Salts of these proteins such as sodium caseinate and calcium caseinate can also be used. Useful polysaccharides to be used for solids surface modification include hydrocolloids such as gum arabic, xanthan, alginate salts, cellulose derivatives, pectin salts, carrageenans, guar gum and mixtures thereof.

It is necessary to achieve an adequate hydration and interaction between the macromolecules and the surface of the solid insoluble in water, for which it is convenient to lower the system temperature at temperatures below 10° C. To induce the polyelectrolytes ionic gelation on the surface of the insoluble solid, a source of polyvalent cations is added to the solids suspension in the presence of the macromolecules. The source of polyvalent cations is preferably a soluble salt or slightly insoluble in water. In a preferred modality, the polyvalent cations source is a $CaCl_2$) solution at a concentration no greater than 2 molar.

Once the macromolecules adsorption process on the surface of the insoluble solid is carried out, the temperature of the system is increased to induce its ionic gelation, which is achieved at temperatures close to 25° C., although in some cases an increase in the temperature of the system of up to 80° C. may be required. The colloidosome suspension is subsequently dried, preferably by spray drying, to generate agglomerated and superficially modified dry solid particles by the ionic gelation process.

The agglomerates of solid particles are redispersed in water, to then generate individual particles by applying disruptive forces such as shear or pressure changes, without excluding others such as cavitation or particles collision. The aqueous suspension of deagglomerated solid particles is used as the emulsifying system of a water insoluble liquid with the application of these same disruptive forces.

The generated emulsion is stabilized by the adsorbed particles in the liquid interface, which confer colloidal and mechanical stability to the emulsion drops. The typical size of emulsion drops is ten times or more the diameter of the stabilizing particle and the emulsified oil ratio: stabilizing particles are between 0.1:1 and 5:1.

Once the emulsion stabilized by particles is generated, the solid particles are fixed to generate a stable shell and, consequently, to produce the colloidosome. For this, a solution of a negatively charged polyelectrolyte previously hydrated is added and, if necessary, cooled to temperatures below 10° C. Subsequently, the formation of a stabilizing film of the particles adsorbed on the emulsion drops is induced by the addition of a divalent cations source.

It is also possible to make the particles fixation by the addition of cross-linking agents, heat treatment, coacervation or other methods. In a preferred modality, the cross-linking agent is selected from the group consisting of alcohols, aldehydes (e.g., glutaraldehyde), vinyls, ketones, proteins and enzymes (e.g., transglutaminase). The particles fixation by heat treatment should induce flocculation or coalescence of the particles on the interface of the emulsion drops.

Once the particles are fixed on the liquid interface, the colloidosomes are dried to generate a colloidosomes dry powder, preferably by spray drying. Other methods such as lyophilization or tray drying are equally viable for the colloidosomes drying. Depending on the conditions of the drying process, individual colloidosomes or colloidosomes agglomerates can be generated. The colloidosomes mechanical stability in the aqueous dispersion makes it possible to preserve the shell integrity during the drying, generating colloidosomes in the form of powder with recovery efficiency greater than 70%.

The following examples illustrate the invention, without the inventive concept being restricted thereto.

EXAMPLES

Example 1. Oleic Acid Colloidosomes Elaboration with Micrometric-Sized Calcium Carbonate Particles 540 g of a sodium caseinate solution (5% w/w) were prepared by hydration for more than 2 hours and cooling to 5° C. and adjusting the pH to 6.5. In parallel, 412 g of a calcium carbonate suspension (67.0% w/w were prepared and average particle size of 3 μm), pH was adjusted to 6.5 and cooled to 5° C. This suspension was mixed with the sodium caseinate solution by mechanical agitation.

Subsequently, 48 g of a calcium chloride solution (4.1% w/w) were added, the temperature of the whole system was increased to 25° C. and dried in a spray dryer at an inlet temperature of 200° C., suction of 40 m$^3$/h, feed pump to 8 mL/min and an incoming air flow to 1200 L/h, to obtain microencapsulated calcium carbonate.

The calcium carbonate dry agglomerated particles were redispersed in water to form a suspension to 30% (w/w) which was subsequently milled in a pearl mill for at least 30 minutes, thus achieving the calcium carbonate agglomerates destruction. FIG. 1 shows the change in particle size of the agglomerated system and the ground system in suspension.

To elaborate the emulsion stabilized with particles, 100 g of the calcium carbonate suspension (30%) were taken of deagglomerated particles, mixed with 15 g of oleic acid, and diluted with water to obtain a system with a 70% of water. This system was homogenized by applying high shear using a rotor stator equipment to 15000 rpm for 10 minutes, after which they were added 0.3 g of CaCl$_2$).

The particles adsorption on the liquid interface was corroborated by optical microscopy (FIG. 2), where the formation of emulsion drops stabilized with calcium carbonate microparticles is evidenced. The particle size distribution of this system is shown in FIG. 3. Then, 100 g of the emulsion stabilized with particles were taken and 3 g of sodium caseinate were added, stirred for 2 hours and cooled to 5° C. Finally, 0.22 g of NaCl were added and the system temperature was increased up to 25° C. The colloidosomes suspension was spray-dried at an inlet temperature of 180° C., suction of 30 m$^3$/h, feed pump with speed of 6 mL/min and incoming air flow of 1000 L/h.

The dry colloidosomes formation was evidenced in the scanning electron microphotographs of FIG. 4. The particle size distribution is presented in FIG. 5. The oleic acid content was corroborated by thermogravimetric analysis (FIG. 6), where an encapsulated content in the colloidosome of approximately 28% was observed.

Example 2. Sunflower Oil Colloidosomes Elaboration with Titanium Dioxide Particles of Sub-Micrometric Size 200 g of titanium dioxide were dispersed in 200 g of a sodium caseinate solution (0.5% w/w), using a cowles-type disperser for 32 minutes at 5° C. To this suspension was added 341 g of a sodium caseinate solution (6.22% w/w) hydrated previously for more than 2 hours and maintaining the temperature of 5° C. and pH adjusted in 6.5, to generate a system with a solids concentration of 30%.

From the previous suspension, 200 g were taken and 32.8 g of a CaCl$_2$) (5.0% w/w) solution, the system temperature was increased 5° C. to 25° C. and dried in a spray dryer with an inlet temperature of 200° C., suction of 40 m$^3$/h, feeding pump with a flow of 8 mL/min and incoming air flow of 1200 L/h, to so obtain microencapsulated titanium dioxide.

The dried agglomerated particles of titanium dioxide were redispersed in water to form a suspension at 30% (w/w), which was later milled in a pearl mill for at least 30 minutes to destroy the titanium dioxide agglomerates. FIG. 7 shows the agglomerated system particle size change and of the milled system.

To make the emulsion stabilized with particles, 100 g of the titanium dioxide suspension (30%) were taken of deagglomerated particles, mixed with 30 g of sunflower oil and the system was homogenized by applying high pressure (1000 bar). The particles adsorption on the liquid interface was corroborated by optical microscopy (FIG. 8), where the emulsion drops formation stabilized with titanium dioxide microparticles is evidenced. The particle size distribution of this system is shown in FIG. 9.

Subsequently, 100 g of the sunflower oil emulsion stabilized with particles were taken and 3 g of sodium caseinate were added. The colloidosomes suspension was spray-dried at an inlet temperature of 180° C., a suction of 30 m$^3$/h, feed pump with speed of 6 mL/min and an incoming air flow of 1000 L/h.

The dry colloidosomes formation could be evidenced by the scanning electron microphotographs shown in FIG. 10, while the particle size distribution is shown in FIG. 11. The content of sunflower oil was corroborated by thermogravimetric analysis (FIG. 12), where sunflower oil encapsulated content in the colloidosome close to 32% was observed.

Example 3. Colloidosomes Elaboration of a Mono and Diglycerides Mixture with Micrometric Calcium Phosphate Particles 540 g of a sodium caseinate solution (5% w/w) were prepared by hydration for more than 2 hours and pH adjustment to 6.5. In parallel, 412 g of a calcium phosphate suspension (67% w/w and average particle size of 3 μm) were prepared and with adjustment of pH to 6.5, which was mixed with the sodium caseinate solution while maintaining mechanical agitation.

Subsequently, 48 g of a CaCl$_2$) (4.1% w/w) solution to 25° C. were dried and the mixture was dried in a spray dryer at an inlet temperature of 200° C., suction of 40 m$^3$/h, feed pump with speed 8 mL/min and an incoming air flow of 1200 L/h, to obtain microencapsulated calcium phosphate.

The calcium phosphate dry agglomerated particles were redispersed in water to obtain a suspension at 25% (w/w), which was then milled in a pearl mill for at least 30 minutes to destroy the calcium phosphate agglomerates. FIG. 13 shows the change in particle size of the agglomerated system and the milled system.

To make the emulsion stabilized with particles, 100 g of the calcium carbonate suspension (25%) of deagglomerated particles were taken and heated up to 55° C. In parallel way 25 g of a mono and diglycerides mixture were heated up to 55° C. and were added slowly to the suspension of deagglomerated particles by applying stirring to 15000 rpm using a rotor-stator equipment.

The particles adsorption on the liquid interface was corroborated by optical microscopy (FIG. 14), where the emulsion drops formation stabilized with calcium phosphate microparticles is evidenced. The particle size distribution of this system is presented in FIG. 15. Finally, 50 g of a 10% sodium caseinate solution (w/w) and 8.0 g of a CaCl$_2$ dihydrate to 5% (w/w) solution.

The colloidosomes suspension is spray-dried at an inlet temperature of 180° C., suction of 30 m$^3$/h, feeding pump with speed of 6 mL/min and incoming air flow of 1000 L/h. The dry colloidosomes formation was evidenced in the scanning electron microphotographs (FIG. 16), with a particle size distribution presented in FIG. 17. The mono and diglyceride content was corroborated by thermogravimetric analysis (FIG. 18), where an encapsulated material content close to 37% was observed.

Example 4. Canola Oil Colloidosomes Elaboration with Particles of Micrometric Kaolin and Reinforced with Fatty Acids 500 g of a suspension were prepared by mixing 200 g of kaolin with 295 g of sodium caseinate solution in a cowles-type disperser at 1000 rpm. To the resulting suspension having 40% of solid material, the pH was adjusted to 6.5 and 166.7 g of a sodium caseinate solution (9% w/w) were added with stirring and 5° C. during 2 hours and 30 g of $CaCl_2$) dihydrate (5% w/w) solution maintaining 5° C. of temperature.

Subsequently, the temperature of the entire system was increased to 25° C. and dried in a spray dryer at an incoming temperature of 200° C., suction of 40 m³/h, feed pump to 8 mL/min and incoming air flow at 1200 L/h. 30 g of solid material obtained by spray drying were taken, dispersed in 70 g of water and stirred for 2 minutes at 15000 rpm using a rotor-stator equipment.

FIG. 19 shows the change in particle size of the agglomerated system and the milled system.

The obtained system was diluted by adding 85 g of water and then 60 g of canola oil were dispersed using a rotor-stator type disperser at 12000 rpm maintaining the stirring for two minutes after the total oil addition. The particles adsorption on the liquid interface was corroborated by optical microscopy (FIG. 20), where the formation of emulsion drops stabilized with kaolin microparticles is evidenced. The particle size distribution of this system is presented in FIG. 21.

To the colloidosomes suspension were added 55 g of sodium caseinate solution (10% w/w) applying stirring at 500 rpm and heating the system between 40° C. and 50° C. for 5 minutes. Then, this system was cooled to 5° C. maintaining the agitation to then adding 8 g of $CaCl_2$) solution dihydrated. The system temperature was increased to 25° C. and spray-dried at an inlet temperature of 180° C., suction 30 m³/h, feeding pump with a speed of 6 mL/min and an incoming air flow at 1000 L/h. The dried product is made up of canola oil drops coated with kaolin particles, as shown in the SEM photomicrographs (FIG. 22).

Alternatively, canola oil colloidosomes with a kaolin particle shell can be reinforced with a fatty shell. For this, an emulsion was prepared using 20 g of a 1:1 mixture by mass of stearic acid/palmitic acid and 180 g of water, homogenized at a temperature above 70° C. for 5 minutes with a rotor-stator disperser (12000 rpm).

100 g of a colloidosomes suspension were taken with 110 g of fatty acids emulsion at 70° C. and by mechanical stir they were dispersed with a disperser (500 rpm) and then cooled to room temperature. Colloidosomes coated with fatty compounds are evidenced in the optical micrograph of FIG. 23.

This system is subsequently brought to a temperature of 5° C., to then continue with the process described above to obtain dry microcapsules reinforced with a layer of saturated fat, as can be seen in the SEM photomicrograph of FIG. 24. The content of canola oil was determined by thermogravimetric analysis (FIG. 25), where a content of encapsulated material close to 36% was observed.

BIBLIOGRAPHICAL REFERENCES

1. Ao, Z.; Li, Z.; Colloidosomes formation by controlling the solvent extraction from particle-stabilized emulsions. Colloids Surfaces A 384, 2011, 592-596
2. Cayre, O.; Noble, P.; Paunov, V. Fabrication of novel colloidosome microcapsules with gelled aqueous core. J. Materials Chemistry, 14, 2004, 3351-3355.
3. Croll, L. M.; Stover, H. D. H. Formation of tectocapsules by assembly and crosslinking of poly(divinylbenzene-alt-maleic anhydride) spheres at the oil-water interface, Langmuir 19, 2003, 5918-5922.
4. Croll, L.; Stover, H.; Hitchcock, A. P. Composite tectocapsules containing porous polymer microspheres as release gates, Macromolecules 38 (2005) 2903-2910.
5. Cui, Y.; van Duijneveldt, J. S. Microcapsules Composed of Cross-Linked Organoclay, Langmuir 28, 2012, 1753-1757.
6. Dinsmore, A. D.; Hsu, M. F.; Nikolaides, M. G.; Marquez, M.; Bausch, A. R.; Weitz, D. A. Colloidosomes: selectively permeable capsules composed of colloidal particles, Science 298, 2002, 1006-1009.
7. Fujiwara, M.; Shiokawa, K.; Araki, M.; Ashitaka, N.; Morigaki, K.; Kubota, T.; Nakahara, Y. Encapsulation of proteins into $CaCO_3$ by phase transition from vaterite to calcite. Crystal Growth Design 10, 2010, 4030-4037.
8. Guillot, S.; Bergaya, F.; de Azevedo, C.; Warmont, F.; Tranchant, J. F. Internally structured pickering emulsions stabilized by clay mineral particles. J. Colloids Interface Sci. 333, 2009, 563-569.
9. He, X. D.; Wang, M. Z.; Zhang, Z. C. The preparation of composite microsphere with hollow core/porous shell structure by self-assembling of latex particles at emulsion droplet interface. J. Colloid Interface Science 299, 2006, 791-796.
10. Laïb, S.; Fabrication of colloidosomes at low temperature for the encapsulation of thermally sensitive compounds. J. Colloid Inter Sci. 317, 2008, 121-129.
11. Liu, G.; Rearrangement of layered double hydroxide nanoplatelets during hollow colloidosome preparation. J. Colloids Interface Sci. 345, 2010, 302-306.
12. Rossier-Miranda, F. J; Schroën, K.; Boom, R. Microcapsule production by an hybrid colloidosome layer-by-layer technique. Food Hydrocolloids 27, 2012, 119-125.
13. Rossier-Miranda, F. J.; Schroën, C. G. P. H.; Boom, R. M. Colloidosomes: Versatile microcapsules in perspective. *Colloids Surfaces A* 343, 2009, 43-49.
14. Sturzenegger, P. N.; Gonzenbach, U. T.; Martynczuk, J.; Size and Microstructure Control of Calcium Aluminate, J. Colloid Interface Science 95, 2012, 2481-2490.
15. Velev, O. D.; Furusawa, K.; Assembly of latex particles by using emulsion droplets as templates. Microstructured hollow spheres, Langmuir 12, 1996, 2374.
16. Wang, X.; Zhou, W.; Cao, J.; Liu, W.; Preparation of core-shell CaCO3 capsules via Pickering emulsion templates. J. Colloid Interface Science 372, 2012, 24-31.

The invention claimed is:

1. A colloidosome-type microcapsule comprising: a water-insoluble oil phase encapsulated in the core, coated by solid microparticles or nanoparticles having macromolecules adsorbed on their surface by ionic gelation, and such microparticles or nanoparticles are fixed together to form a stable shell.

2. The colloidosome-type microcapsule according to claim 1, comprising one or more compounds incorporated in the water-insoluble phase of the microcapsule with shell formed by microparticles or nanoparticles.

3. A process for elaborating colloidosomes-type microcapsules comprising:

a) dispersing in water agglomerates of solid microparticles or nanoparticles having macromolecules adsorbed on their surface obtained by ionic gelation, to form a suspension;
b) emulsifying an oily liquid insoluble in water using the suspension obtained in a) as emulsifier; and
c) fixing the adsorbed microparticles or nanoparticles on the water—oily liquid insoluble in water interface, to obtain the colloidosomes.

4. The process according to claim 3, wherein the mixture obtained in c) is dried to obtain powder colloidosomes.

5. The process according to claim 3, wherein the microparticles or nanoparticles of step a) comprise water-insoluble solids selected from the group consisting of metallic and non-metallic minerals, phyllosilicates, polymer particles, and insoluble solids obtained via synthesis, extraction or by bioprocesses.

6. The process according to claim 3, wherein the solid microparticles or nanoparticles of step a) have a size between 10 nm and 1000 µm.

7. The process according to claim 3, wherein shear-type disruptive forces, cavitation, shock, pressure drop or combinations thereof are applied in step a) to prevent agglomerates formation.

8. The process according to claim 3, wherein fixation of step c) is carried out by polyelectrolytes adsorption, cross-linking, heat treatment and/or treatment with a fatty acid emulsion or fatty acids mixture.

9. The process according to claim 8, wherein fixation of step c) is carried out by polyelectrolytes adsorption.

10. The process according to claim 9, wherein the polyelectrolytes adsorption is carried out by addition of a polyvalent cations source to the aqueous suspension and of a solution of a polyelectrolyte negatively charged to the stabilized emulsion and decreasing the temperature from 25° C. to 5° C.

11. The process according to claim 10, wherein the polyvalent cations source is a water-soluble calcium salt.

12. The process according to claim 10, wherein the polyelectrolyte is selected from the group consisting of proteins and their derivatives, polysaccharides and synthetic polymers.

13. The process according to claim 10, wherein the polyelectrolyte is sodium caseinate.

14. The process according to claim 8, wherein fixation of step c) is carried out by cross-linking.

15. The process according to claim 14, wherein cross-linking is performed by incorporating a cross-linking agent into the aqueous phase or in the non-aqueous phase.

16. The process according to claim 15, wherein the cross-linking agent is selected from the group consisting of alcohols, aldehydes, vinyls, ketones, proteins, and enzymes.

17. The process according to claim 16, wherein the cross-linking agent is glutaraldehyde or transglutaminase.

18. The process according to claim 8, wherein fixation of step c) is carried out by treatment with a fatty acid emulsion or fatty acids mixture.

19. The process according to claim 18, wherein the fatty acid emulsion or fatty acid mixture corresponds to fatty acids with hydrocarbon chain of 10 or more carbons.

20. A colloidosome-type microcapsule obtained by the process according to claim 3.

* * * * *